(12) United States Patent
Bonnet

(10) Patent No.: US 6,482,205 B1
(45) Date of Patent: Nov. 19, 2002

(54) BIPOLAR FORCEPS

(75) Inventor: Ludwig Bonnet, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/556,606

(22) Filed: Apr. 21, 2000

(30) Foreign Application Priority Data

Apr. 27, 1999 (DE) ......................................... 199 19 072

(51) Int. Cl.[7] .............................................. A61B 18/18
(52) U.S. Cl. ...................................................... 606/51
(58) Field of Search .......................... 606/41, 45, 48, 606/50, 51, 52

(56) References Cited

U.S. PATENT DOCUMENTS

| | | |
|---|---|---|
| 2,031,682 A | 2/1936 | Wappler et al. |
| 5,258,006 A | 11/1993 | Rydell et al. |
| 5,269,780 A | 12/1993 | Roos |
| 5,484,435 A * | 1/1996 | Fleenor et al. ............... 606/46 |
| 5,626,578 A * | 5/1997 | Tihon ......................... 606/482 |
| 5,891,141 A * | 4/1999 | Rydell ......................... 606/452 |
| 6,273,887 B1 * | 8/2001 | Yamauchi et al. ............. 606/48 |

FOREIGN PATENT DOCUMENTS

| | | |
|---|---|---|
| DE | 39 17 328 C2 | 3/1991 |
| DE | 41 30 064 C2 | 6/1993 |
| DE | 43 03 882 C2 | 2/1995 |

* cited by examiner

Primary Examiner—Linda C. M. Dvorak
Assistant Examiner—Daniel Ruddy
(74) Attorney, Agent, or Firm—Akin, Gump, Strauss, Hauer & Feld, L.L.P.

(57) ABSTRACT

The forceps serves for coagulating and severing the body tissue of a patient by way of a forceps jaw which consists of two jaw parts, is actuatable with a proximate handle for opening and closing and is located at the distal forceps end, wherein on the distal end section of a first jaw part a hook projects towards the second jaw part, said hook fixing the tissue, grasped between the jaw parts given a closed forceps jaw, in the forceps jaw. On the first jaw part additionally there is provided a proximally running web which proceeds directly from the hook and projects in the direction of the second jaw part.

5 Claims, 1 Drawing Sheet

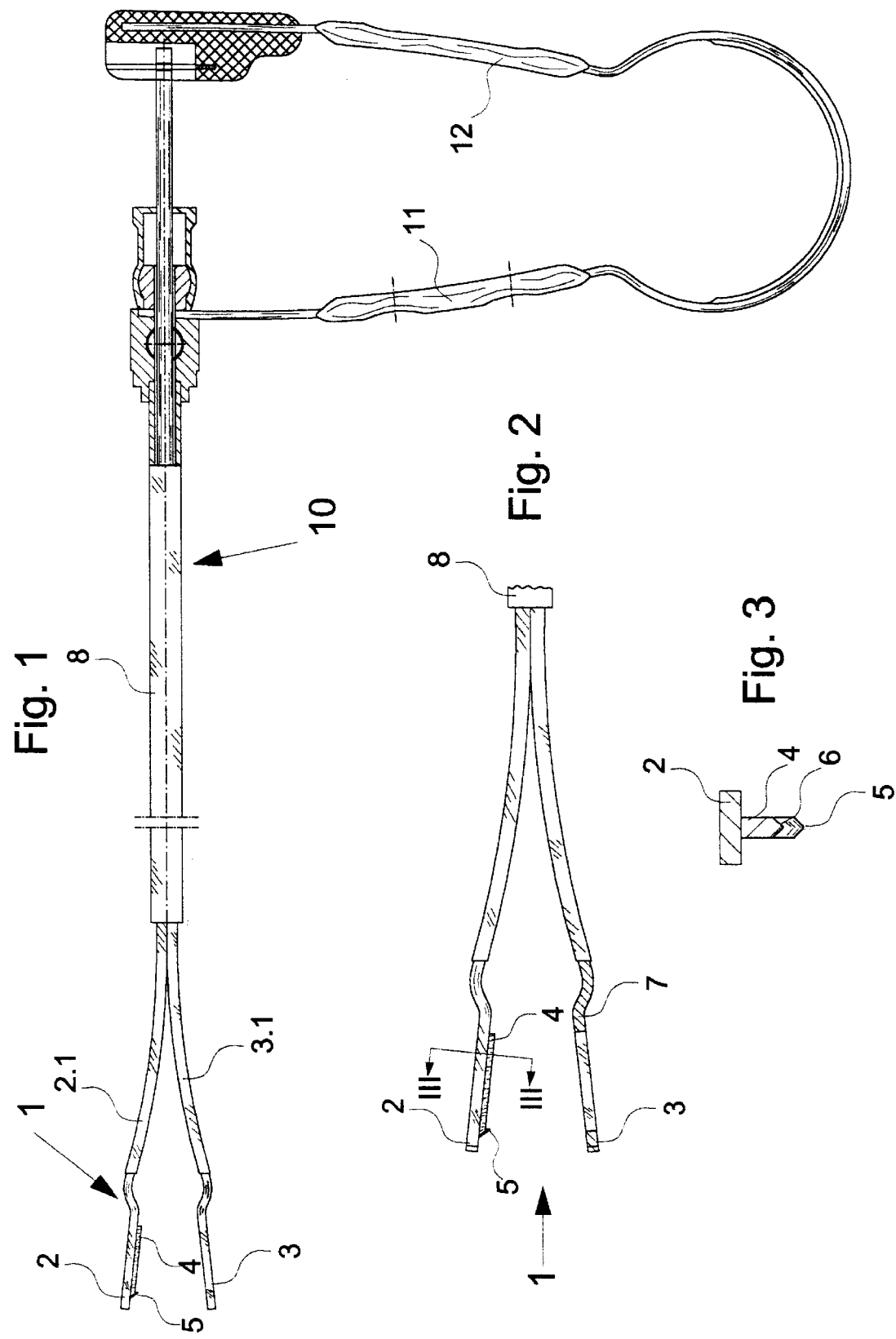

BIPOLAR FORCEPS

BACKGROUND OF THE INVENTION

The invention relates to a bipolar forceps for coagulating and severing the body tissue of a patient by way of a forceps jaw which consists of two jaw parts, which is actuatable with a proximate handle for opening and closing and which is located at the distal forceps end, wherein on the distal end section of a first jaw part a hook projects towards the second jaw part, said hook fixing the tissue, grasped between the jaw parts given a closed forceps jaw, in the forceps jaw.

With such an electro surgical bipolar forceps (U.S. Pat. No. 4,418,692) the tissue to be coagulated, of e.g. tubes in the inside of the body are grasped between the jaw parts. These are formed as bipolar electrodes and are run through with a high-frequency current which causes the tissue located between the electrodes to be coagulated.

Thereafter tissue locations coagulated in this way are severed with a scissors. The exchange of instruments caused by way of this is annoying and also timeconsuming and by way of the lengthening of the operation time leads to unnecessary burdening of the patient and operating personnel. The surgeon may under certain circumstances also briefly lose the orientation during the exchange of instrument.

Improved are the forceps with an integrated knife (EP 0 210 125 A1, U.S. Pat. No. 5,445,638), the knife however must be actuated separately after the coagulation procedure. Furthermore forceps equipped with knives or scissors are quite complicated in their construction.

The object of the invention lies in providing a bipolar forceps with which the coagulation and the severing of tubular organs and also fine tissue structures may be carried out with a single instrument without a change of instrument and without an additional actuation of a cutting tool.

This object with bipolar forceps according to the known type is achieved according to the invention in that on the first jaw part additionally there is provided a proximally running web which proceeds directly from the hook and projects in the direction of the second jaw part.

With the application of such a forceps the tissue grasped between the jaw parts is coagulated. Subsequent to this, tissue which has become brittle by way of the coagulation and which particularly in the region of the edges of the web on account of the high current density is carbonized, inasmuch as this has not already been effected, with the forceps jaw remaining closed is completely broken open and severed in that the forceps jaw is simply pulled somewhat proximally, wherein the hook effects the breaking open of the tissue or at least supports this and other-wise has the purpose of preventing the sliding out of the tissue from the forceps jaw.

With a preferred embodiment form the hook and the web form one piece and the hook projects towards the second jaw part beyond the web. The web and the first jaw part are in cross section T-shaped, wherein the web at its free cross sectional end forms at least one sharp longitudinally running edge. Furthermore the second jaw part has a recess which may essentially completely accommodate the hook and the web given a closed jaw part in the case that no tissue is located between the jaw parts. Furthermore the contour of the recess is adapted to the contour of the web surface which lies opposite the second forceps jaw or the recess. If thus this web surface is rectangular usefully also the recess will have a rectangular contour so that in this case two sharp longitudinal edges are present on the web on which there is given a particularly high density of the current flowing from the web to the second jaw part via the tissue.

BRIEF DESCRIPTION OF THE DRAWINGS

The invention is hereinafter described by way of an embodiment example shown in the drawing. There are shown:

FIG. 1: schematically a lateral view of a forceps according to the invention in a part section, FIG. 2: the distal end of the forceps according to FIG. 1 in an enlarged representation and FIG. 3: enlarged a section according to section line III—III in FIG. 2 through the distal end of the first jaw part.

DETAILED DESCRIPTION OF THE INVENTION

The forceps 10 shown in FIG. 1 has at its distal end a forceps jaw 1 with a first jaw part 2 and a second jaw part 3 of electrically conducting material. Axial extensions or branches 2.1 and 3.1 on both jaw parts are displaceable in a shank tube 8. This is effected by a resilient handle which consists of two grip parts 11 and 12 and which is provided at the proximate end of the forceps. If the grip parts 11 and 12 are pressed together the branches 2.1, 3.1 move distally wherein the branches resiliently spread apart for opening the jaw part. If on the other hand the handle is unloaded, the branches slide proximally into the shank tube 8 with the result that the forceps jaw is closed. These functions which are also possible with differently formed handles are known (DE 23 25 626 A1 and U.S. Pat. No. 4,418,692) and thus do not need to be described any further.

Via connections which are not shown, in a likewise known manner, to the jaw parts 2, 3 functioning as bipolar electrodes of the forceps there may be supplied a high-frequency electrical current which serves for coagulating the tissue grasped between the jaw parts 2, 3. Otherwise in a likewise common manner the branches 2.1, 3.1 guided in the shank tube 8, up to the vicinity of the jaw parts 2, 3 are insulated from one another and also with respect to the metallic shank tube 8 by way of insulating coatings.

FIG. 2 clearly shows that at the distal end section of the first jaw part 2 there is shown a hook 5 which projects towards the second jaw part 3 and serves for fixing the tissue, grasped between the jaw parts given a closed forceps jaw 1, in the forceps jaw. From the hook 5 proximally and parallel to the first jaw part 2 there runs a straight web 4 of electrically conducting material protruding towards the second jaw part 3. Usefully the book 5 and the web 4 form a premanufactured piece which is attached to the first jaw part 2.

By way of FIG. 2 it is furthermore to be recognized that the hook 5 projects beyond the side, of the web 4, which faces towards the second jaw part 3 in order thus to prevent the tissue grasped between the jaw parts 2, 3 on the one hand from sliding out of the closed jaw part, and on the other hand to also support the function of the separation or breaking up of the coagulated tissue. Furthermore the second jaw part 3 has a recess 7 which with a closed forceps jaw may essentially completely accommodate the hook 5 and the web 4, if there is not tissue between the jaw parts. This above all is useful because in this way a secure grasping of the tissue to be coagulated in the region of the web 4 is possible.

FIG. 3 shows that the first jaw part 2 together with the web 4 seen in cross section forms the shape of a T and that the free edge 6, of the web 4, which protrudes towards the second jaw part 3 is formed sharp.

By way of this longitudinal edge 6 a high current density of the current flowing via the web and the tissue to the second jaw part is achieved and thus the definition of a tighly limited coagulation region of the tissue clamped between the two jaw parts is possible. As already mentioned in the introduction the web 4 in cross section may also be formed rectangular so that on the web there are formed two sharp longitudinal edges.

After the coagulation the brittle and partly carbonized tissue, inasmuch as this has not already been effected may be completely separated in that the forceps jaw is displaced proximally by way of a suitable actuation of the handle.

The procedures of the coagulation and the severing of the tissue are effected accordingly in one or where appropriate two operating steps. Firstly thus the tissue is coagulated, whilst subsequent to this, inasmuch as it has not already been effected, the coagulated tissue is severed with the aid of the hook. With this the partly opened forceps jaw may be moved proximally. Furthermore the procedure of the breaking up or severing the coagulated tissue may be supported by a slight lifting of the forceps.

What is claimed is:

1. A bipolar forceps for coagulating and severing body tissue of a patient, the forceps comprising a forceps jaw having a first jaw part and a second jaw part lying opposite the first jaw part, the forceps jaw being located at a distal end of the forceps and being actuatable with a proximate handle for opening, closing and axial movement of the forceps jaw, wherein at least one of the first jaw part and the second jaw part forms an electrode of the forceps, wherein the first jaw part includes a hook on its distal end, the hook projecting toward the second jaw part and being capable of fixing body tissue grasped between the first jaw part and the second jaw part when the forceps jaw is closed, the hook further being capable of separating coagulated body tissue when the forceps jaw is moved axially in a proximate direction by movement of the proximate handle, wherein the first jaw part further includes a web which runs proximally directly from the hook and projects toward the second jaw part.

2. The forceps according to claim 1, wherein the web and the second jaw part each forms an electrode of the forceps.

3. The forceps according to claim 1, wherein the hook and the web form one piece and the hook projects beyond the web toward the second jaw part.

4. The forceps according to claim 1, wherein the web and the first jaw part together are T-shaped in cross section and the web has at least one sharp edge at its free cross sectional end.

5. The forceps according to claim 1, wherein the second jaw part has a recess which substantially accommodates the hook and the web when the forceps jaw is closed and no tissue is located between the jaw parts.

* * * * *